United States Patent [19]

Mehta et al.

[11] Patent Number: 5,002,689

[45] Date of Patent: Mar. 26, 1991

[54] PREPARATION OF ORGANOMETALLIC AMIDE COMPOSITIONS

[75] Inventors: Vijay C. Mehta; Terry L. Rathman; Conrad W. Kamienski; Robert C. Morrison, all of Gastonia; Randy W. Hall, Kings Mountain, all of N.C.

[73] Assignee: Lithium Corporation of America, Gastonia, N.C.

[21] Appl. No.: 160,371

[22] Filed: Feb. 25, 1988

[51] Int. Cl.$^5$ .............................................. C09K 3/00
[52] U.S. Cl. .............................................. 252/182.12
[58] Field of Search ........... 252/182.3, 182.14, 182.12; 502/153, 156, 157

[56] References Cited

U.S. PATENT DOCUMENTS

| | | | |
|---|---|---|---|
| 3,903,169 | 9/1975 | Bader et al. | 260/590 |
| 3,925,449 | 12/1975 | Teuber et al. | 260/465.5 R |
| 4,128,501 | 12/1978 | Smith et al. | 502/153 |
| 4,139,490 | 2/1979 | Halasa et al. | 502/153 |
| 4,165,330 | 8/1979 | Whitney et al. | 260/448.2 B |
| 4,263,217 | 4/1981 | Malpasi et al. | 252/182 |
| 4,595,779 | 6/1986 | Morrison et al. | 564/463 |

OTHER PUBLICATIONS

House, H. O. et al., J. Org. Chem., 43, No. 4, p. 700, (1978), *Chemistry of Carbanions.31 Cyclization of the Metal Enolates from ω-Bromo Ketones.*

Alberella, J. P., J. Org. Chem., 42, No. 11, p. 2009, (1978), *A Convenient Method for the α-Carbethoxylation of Alkylnitriles.*

Schlosser et al., Chem. Ber., 102, p. 1944, (1969), *Die Fluorolyse Metallorganischer Bindungen durch Perchlorylfluorid.*

Reetz, M. T. et al., Liebigs Ann Chem., 1471, (1980), *Einfache Darstellung von Lithiumdiisoporpylamid in molarem Maβstab.*

Bates, R. B. et al., J. Org. Chem., 37, No. 4 (1972), *Cycloreversions of Anions from Tetrahydrofurans. A Convenient Synthesis of Lithium Enolates of Aldehydes.*

Honeycutt, S. C., J. Organometallic Chem., 29, 1, (1971), *Kinetics of the Cleavage of Tetrahydrofuran By n-Butyllithium in Hydrocarbon Solvent.*

Bartlett, P. D. et al., J. Org. Chem. Soc., 75, 1771 (1953), *The Reaction of Isopropyllithium and t-Butyllithium With Simple Olefins.*

Spialter, L. et al., J. Org. Chem., 31, 4263 (1966), *2-Cyclohexylethyltricyclohexylsilane. Formation of Cyclohexylethyllithium From the Cleavage of Ethyl Ether by Cyclohexyllithium.*

Richey, H. G. et al., J. Org. Chem., 48, 4349 (1983), *Reactions of Primary Amines with Organolithium Compounds.*

Coates, G. E. et al., J. Chem. Soc. A, (1967), *Some Amino-alkylmagnesium Complexes: Evidence for Three--co-ordinate Magnesium.*

Ashby, E. C. et al., J. Org. Chem., 43, No. 25, 4750 (1978), *A New Convenient, and Stereospecific Method for the Conversion of Secondary Amines to Primary Amines and Olefins. Thermal Decomposition of Magnesium, Zinc, and Aluminum Amides.*

Lochmann, L. et al., J. Organometallic Chem., 179, 123 (1979), *Reactions of Substituted N-Lithium Amides With Heavier Alkali Metal Alkoxides. A Novel Method for the Preparation of N-Sodium and N-Potassium Dialkylamides.*

Ashby, E. C. et al., J. Org. Chem., 43, No. 8, 1564 (1978), *reactions of Magnesium Hydrides. 3. Stereoselective Reduction of Cyclic and Bicyclic Ketones by Dialkylaminomagnesium Hydrides.*

*Primary Examiner*—Edward A. Miller
*Attorney, Agent, or Firm*—Charles C. Fellows; Robert L. Andersen

[57] ABSTRACT

This invention concerns organometallic amide compositions particularly bimetallic organoamides in liquid hydrocarbon solutions in which one metal is an alkali metal the other an alkaline earth metal, zinc or copper and particularly lithium magnesium bis-diorganoamides, such as lithium magnesium bis-diisopropylamide and processes for preparation of such amides. These novel bimetallic amides have increased solubility in liquid hydrocarbon solvents and improved thermal and precipitation stability at temperatures of 0° C. to 40° C.

7 Claims, No Drawings

PREPARATION OF ORGANOMETALLIC AMIDE COMPOSITIONS

The present invention concerns novel mono- and bimetallic organoamide compositions, their stable solutions in liquid hydrocarbon solvents, and in hydrocarbon solvents containing small amounts of a Lewis base and improved methods for their production.

The bulky organoamides of alkali metals are used extensively as reagents in organic synthesis by virtue of the combination of their strong Bronsted basicity and low nucleophilicity. Lithium organoamide compounds such as lithium diisopropylamide (LDA), lithium pyrrolidide (LPA), and lithium hexamethyldisilazide (LHS) are essentially insoluble in Lewis base-free hydrocarbon solvents. Although these compounds are soluble in ethers, they are quite unstable with time even at room temperature. Thus, users of these compounds (especially LDA) prepare their own requirements immediately before use by the reaction of a pyrophoric solution of n-butyllithium with amine in ether medium or reaction of lithium metal with diisopropylamine in ether medium.

Lithium diisopropylamide (LDA) has previously been synthesized by reacting lithium metal and styrene with diisopropylamine in ethyl ether (R. Reetz and F. Marrier, Liebigs Am. Chem., 1471, 1980). However, LDA in ether solvents is not stable. Further modifications were reported and patented in the synthesis of a "stable" solution of LDA in hydrocarbon solvent containing a limited amount of THF by Morrison et al. (U.S. Pat. No. 4,595,779, June 17, 1986). The main drawback of LDA in ether solution or in a hydrocarbon solution containing even limited THF (i.e., $\leq 1.0$ mole/mole LDA) is its limited thermal stability. These solutions of LDA complexed with limited THF ($\leq 1.0$ mole/mole LDA) do lose a significant amount of their activity (25 to 50%) on storage at 30° C.–40° C. for 30 days, although no loss is detected at 0° C. to 10° C. Crystallization occurs from solution at $\leq 0°$ C. when the concentration of LDA and THF is 2.0 molar. Thus, there continues to be a demand for organometallic amide solutions in hydrocarbon solvents with improved thermal stability.

The present invention provides stabilized, nonpyrophoric solutions of an alkali metal diorganoamide in a liquid hydrocarbon solvent containing a Lewis base, such as tetrahydrofuran, and 1 to 10 mole percent of a metallic diorganoamide. These compositions are conveniently represented as a composition of the formula:

$$M_x^a M_y^b (M^c RR')_z \cdot nLB \cdot mM^d X$$

wherein
$M^a$ = alkali metals (gr IA the Periodic Table, e.g., Li, Na, K . . . )
$M^b$ = alkaline earth metals (gr IIA of Periodic Table, such as Mg, Ca, Ba, Sr, and also other metals such as Zn, Al, and Cu)
$M^c$ = N, P, and As
$M^d$ = lithium
R = alkyl, cycloalkyl, aryl, alkylaryl, aralkyl, trialkylsilyl, heteroalkyl, heteroaryl, etc.
R' = alkyl, cycloalkyl, aryl, alkylaryl, aralkyl, trialkylsilyl, heteroalkyl, heteroaryl, and hydrogen . . .
X = halogen (Cl, Br, I), trifluoromethylsulfonyl, p-methylbenzenesulfonyl (p-tosyl), and perchlorate ($ClO_4$)
m = 0 to 2
n = >0 and <4.0
x + y = 1
z = x + (y multiplied by the valence of metal $M^b$)
LB = Lewis base such as tetrahydrofuran (THF), methyl THF, dimethyl ether, diethyl ether, dibutyl ether, tertiary amines such as trimethylamine, triethylamine, tetramethylethylenediamine . . .

The Lewis base to amide ratios are critical to the solubility and stability of the compositions represented by the foregoing formula. In general, 1 to 2 moles of Lewis base, such as THF, will solvate each mole of bimetallic diorganoamide. An additional important aspect of this invention is the discovery that a lithium halide dissolved in the bimetallic diorganoamide solution increases solution stability of the diorganoamide. However, two moles of Lewis base are necessary to dissolve a mole of lithium halide. Many metallic diorganoamides, such as magnesium bis-diisopropylamide, are hydrocarbon soluble. Thus, the ratio of $M^a$ to $M^b$ in the formula affects the amount of Lewis base required to dissolve a specific bimetallic diorganoamide.

The Lewis base to amide ratios in the foregoing formula are determined by the value of n which must reflect the variables of the $M^a$ to $M^b$ ratio and whether lithium halide is included in the solution. When there is no lithium halide in the solution the value for n can vary between greater than zero and less than three. The value for n when there is no lithium halide in a solution in a metallic diorganoamide solution is related to the value z so that n equals z multiplied by a value between 1 to 2, i.e., n = z (1.5 ± 0.5). When there is lithium halide in the solution, the value of n is appropriately related to the value m so that n is equal to m multiplied by the value of x plus 2, i.e., $n = m(2 + x)$. When the value for y is zero and a mono-metallic diorganoamide containing lithium halide is present, the value of n is equal to the value of m multiplied by two plus one, i.e., $n = 2m + 1$.

The process of this invention provides hydrocarbon solutions of bimetallic organoamide compositions. Broadly, the process reacts a metallic bis-mono- or diorganoamide composition or an organoamidometallic halide composition with an alkali metal and a mono- or diorganoamine at about 0° C. to about 50° C. in a hydrocarbon solvent in the presence of an electron carrier and a Lewis base to produce the desired bimetallic mono- or diorganoamide composition. One of the metals is thus an alkali metal such as lithium, sodium or potassium and the other metal is selected from alkaline earth metals such as magnesium, calcium, barium, etc., and other metals such as zinc, aluminum and copper.

One aspect of the invention begins with the preparation of an alkaline earth bis-diorganoamide, such as magnesium bis-diisopropylamide (MDA), which is to be employed in the subsequent preparation of the stable bimetallic diorganoamide compositions of the invention, such as, for example, a lithium/magnesium diisopropylamide composition.

The preparation of said magnesium bis-diorganoamide can be accomplished by a number of methods.

One novel method of this invention comprises reaction of magnesium metal with n-butyl chloride in the presence of a stoichiometric amount of diisopropylamine in a hydrocarbon medium to yield a solid intermediate product, diisopropylamidomagnesium chloride, as shown in equation (1), in which "iPr" represents isopropyl.

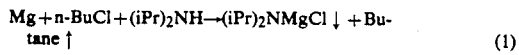

(1)

The product is then reacted further with lithium metal, styrene or isoprene (as carrier for lithium in the reaction), and more diisopropylamine in the presence of not more than 0.5 moles of tetrahydrofuran (THF) per mole of lithium employed, to produce the desired magnesium bis-diisopropylamide dissolved in the hydrocarbon (H.C.) solvent and a precipitate of lithium chloride as shown in equation (2).

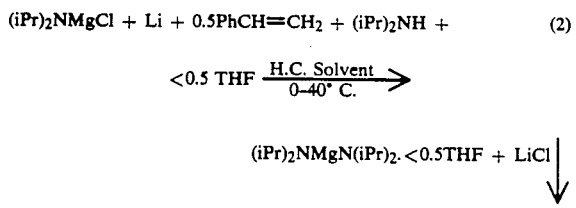

(2)

The reaction of lithium metal, styrene and diisopropylamine produces "in situ" a soluble lithium diisopropylamide as the intermediate which reacts with diisopropylamidomagnesium chloride to form soluble magnesium bis-diisopropylamide and insoluble lithium chloride The requirement for use of less than 0.5 moles of THF per mole of lithium metal used is to prevent solubilization of said lithium chloride in the solution of magnesium bis-diisopropylamide. Obviously the use of greater quantities of THF leads to the dissolution of all LiCl in the hydrocarbon solvent, also a novel aspect of this invention.

In order to eliminate the limitation for the requirement of <0.5 moles of THF/Li in the preparation of magnesium bis-diisopropylamide, one may substitute sodium metal for the lithium metal employed. The resulting sodium chloride by-product is insoluble in such product solutions even in the presence of more than one mole of THF/NaCl.

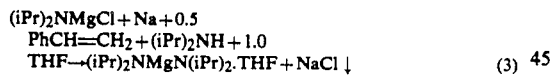

(3)

One procedure for preparing magnesium bis-diisopropylamide in liquid hydrocarbon solvents containing no Lewis bases, such as THF, involves the use of preformed alkyllithium compounds, such as n-butyllithium, which require no THF, as reactants for diisopropylamidomagnesium chloride in place of the "in-situ" directly formed lithium diisopropylamide of equation (2) which does require THF. Although this method will also produce a form of magnesium bis-diisopropylamide useful in the subsequent preparation of the bimetallic diorganoamides of this invention, the process is wasteful of lithium metal since the formation of butyllithium requires the use of two equivalents of lithium metal per mole of butyllithium formed, whereas only one equivalent of lithium is required in the process of equation (2).

Other variations to produce the magnesium bis-diorganoamides of the invention are possible, including direct reaction of lithium and magnesium metals with alkyl halides in hydrocarbon solvents in the presence of limited amounts of Lewis bases such as tetrahydrofuran (THF) to form dialkylmagnesium compounds followed by addition of two equivalents of diisopropylamine as shown in equation (4).

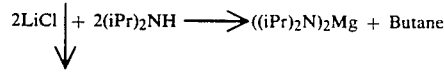

(4)

Again, however, reactions of this type are wasteful of expensive lithium metal.

The hydrocarbon solutions of magnesium bis-diorganoamides produced by the novel method of the invention [equations (1), (2) and (3) above], are highly stable and soluble at temperatures between 0° and 40° C. with a loss of less than 5 mole % in four weeks at 40°. Magnesium bis-diisopropylamide produced by the invention is soluble to the extent of 1 mole per liter and higher as compared to the same product made in an ether-free solution from n-butyllithium which has a maximum solubility of 0.7 molar at ambient or room temperatures.

Stable and soluble bimetallic lithium magnesium diorganoamide compositions are prepared in liquid hydrocarbon solvents according to the invention starting with magnesium bis-dialkylamides using a reaction scheme exemplified by the following equation for the preparation of lithium magnesium diisopropylamide compositions:

yMDA + xLi + xiPr₂NH + 0.5 × Styrene + (5)

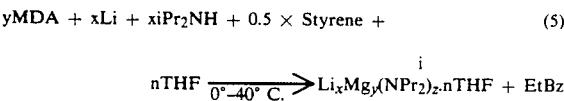

The reaction sequence shown in equation (5) can be used at all possible values of x and y, so as to produce lithium magnesium diisopropylamide compositions with x/y ratios varying from about 0.01 to 99. However, the magnesium bis-diisopropylamide required for this reaction must be made in a separate reactor if the ratio of x/y in the product is to be 0.5 or higher because of the need to separate attendant LiCl by-product, in order to avoid solubilization problems encountered later on in the lithium diisopropylamide preparation step. This is also described above for the preparation of magnesium bis-diisopropylamide made using lithium metal [equation (2)].

The lithium metal reaction with diisopropylamine in equation (5) remains vigorous at 0°-40° C. in the presence of even small amounts of magnesium bis-diisopropylamide (MDA) in contradistinction to the reaction of lithium metal in the absence of MDA which proceeds well only at a temperature of 35° C. and above.

In equation (5), n (number of moles of THF) must be equal to or greater than x (mole fraction of lithium) in order to form x number of moles of lithium diisopropylamide.

If the desired ratio of x/y in the product is less than 0.5, then the reaction can be carried out directly in one pot using diisopropylamidomagnesium chloride [equation (1)], since, although at least one mole of LiCl is formed for every 1.5 moles of lithium metal employed, the THF requirement to produce 0.5 mole (or less) of LDA is less than half that needed to dissolve LiCl according to equation (6).

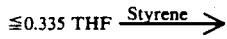

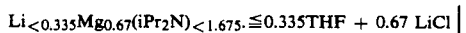

A preferred ratio of x/y in the product is less than 0.3 in order to completely eliminate the presence of dissolved LiCl in the product. However, if the ratio of x/y in the product is greater than 0.5, this process will unexpectedly yield a soluble bimetallic organoamide composition containing dissolved lithium chloride, the amount of which depends upon x/y. Thus, for example, when x/y in the product is 2.0, and the required amount of THF is employed then all of the lithium chloride formed will be soluble. Other halide precursors to the lithium salt can be prepared, such as diisopropylaminomagnesium bromide.

Substitution of sodium for lithium as the chloride scavenger in the above reaction, and as shown in equation (3) above, allows the preparation of halide-free bimetallic organoamide products with x/y ratios greater than 0.5, since the NaCl by-product formed remains insoluble even in the presence of at least one mole of THF as shown in equation (7).

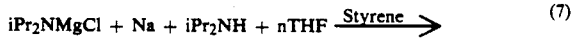

Values of n can be equal to 1 or higher without any danger of solubilizing the chloride salt.

Total substitution of sodium for lithium in equation (6) can also be effected leading to stable, soluble, halide-free sodium magnesium diorganoamide compositions, $Na_xMg_y(NR_2)_z \cdot nTHF$, even at x/y ratios of 1 and higher, for example:

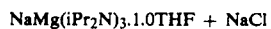

Thus, a one pot reaction can be utilized to produce the sodium magnesium diorganoamide compositions at all x/y ratios directly from magnesium and sodium metals (2 step reaction), a distinct advantage over the comparable lithium route, where x/y in the product is limited to less than 0.5. As noted earlier [see equation (5)], lithium magnesium diorganoamide compositions in which x/y is greater than 0.5 require the prior preparation (separate pot or reactor) of the chloride-free magnesium diorganoamide.

It should be noted that the sodium route requires the use of a full equivalent of styrene per alkali metal atom, whereas the lithium route requires the use of only a half of one equivalent of styrene per alkali metal atom.

In place of diisopropylamine as the diorganoamide precursor, one may substitute a wide variety of diorganoamines. Generally, these are $C_2$–$C_{18}$ linear and branched dialkylamines such as, e.g., dimethylamine, diethylamine, di-n-propylamine, ethyl-n-propylamine, di-n-butylamine, ethyl-n-butylamine, di-n-hexylamine, n-butyl-n-hexylamine, di-n-octylamine, n-butyl-n-octylamine, di-2-ethylhexylamine, ethyl-2-ethylhexylamine, diisoamylamine, di-tert-butylamine, di-sec-butylamine, and so forth.

Along with and in admixture with the above-described diorganoamine precursors, one may also utilize $C_2$–$C_{18}$ linear and branched monoalkylamines, such as, e.g., methylamine, ethylamine, n-propylamine, isopropylamine, n-butylamine, isobutylamine, tert-butylamine, n-hexylamine, 2-ethylhexylamine, and the like. Thus, in the general composition formula first written above, the organic groups represented in the formula by R and R' include $C_2$ to $C_{18}$ linear and branched groups.

Also contemplated are carbocyclic amines or mixtures thereof with the above-mentioned acyclic amines such as, e.g., cyclopentylamine, dicyclopentylamine, cyclohexylamine, dicyclohexylamine, methylcyclohexylamine, isopropylcyclohexylamine, phenylamine (aniline), diphenylamine, methyl-phenylamine, ethyl-phenylamine, benzylamine, o-tolylamine, dibenzylamine, phenethylamine, methyl-p-tolylamine, p-t-butylphenylamine, and the like.

In addition, one may employ heteroalkyl or heterocycloalkyl or heteroaryl amines such as, e.g., hexamethyldisilazane, piperidine, pyrollidine, 2,2,6,6-tetramethylpiperidine, 8-aminoquinoline, pyrrole, 3-methylaminopyridine, 2-methoxyethyl-methylamine, 2-dimethylaminoethyl-methylamine, 2-trimethylsilylethyl-ethylamine, 3-dimethylaminopropyl-ethylamine, 3-dimethylphosphinobutyl-methylamine, and the like.

The liquid hydrocarbon solvents useful in practicing this invention are typically selected from aliphatic hydrocarbons containing 5 to 10 carbon atoms, alicyclic hydrocarbons containing 5 to 10 carbon atoms and aromatic hydrocarbons containing 6 to 10 carbon atoms. Exemplary of these liquid hydrocarbon solvents are pentane, n-hexane, n-heptane, mixed paraffinic hydrocarbons having boiling points below about 130° C., cyclohexane, methylcyclohexane, benzene, toluene, ethylbenzene, xylene, cumene and so forth. The compositions of this invention produced by the process employing styrene or isoprene will include as part of the hydrocarbon system, the reduced alkali metal or electron carrier; ethylbenzene (EtBz) where styrene was used as the carrier and 2-methyl-2-butene where isoprene is used. Other suitable electron carriers may include butadiene, divinylbenzene and napthalene, for example.

Contemplating the invention even more broadly, one may substitute other group VA elements for nitrogen in the organoamide portion of the metal organoamide composition, such as, for example, phosphorus or arsenic. Thus, instead of organoamine precursors for such metal organoamide compositions, one may employ organophosphine precursors for metal organophosphide compositions. Thus, for example, one employs dimethylphosphine, diethylphosphine, tert-butylphosphine, phenylphosphine, cyclohexylphosphine, diisopropylphosphine, dioctylphosphine, and the like, in place of the corresponding amines listed above to satisfy $M^cRR'$ in the formula $$M_x{}^a M_y{}^b (M^cRR')_z \cdot nLB \cdot mM^dX$$

$M^a$ metals in the above general formula $M_x{}^aM_y{}^b(M^cRR')_z \cdot nLB \cdot mM^dX$ are alkali metals of Group IA of the Periodic Table, such as lithium, sodium, potassium, cesium, and rubidium, but most preferably lithium and sodium. These metals can be employed in a variety of shapes and sizes, for example, as dispersions (in hydrocarbon media), sand, shot, chips or wire; but, for the most efficaceous results, one generally employs the finely divided metals (less than 100 micron particle size) dispersed in a hydrocarbon medium, such as heptane, cyclohexane, methylcyclohexane, or light mineral oil to keep the surface of the metal particles protected during handling operations.

$M^b$ metals in the above general formula $M_x{}^aM_y{}^b(M^cRR')_z \cdot nLB \cdot mM^dX$ are alkaline earth metals of Group IIA of the Periodic Table, such as beryllium, magnesium, calcium, strontium, and barium, and most preferably magnesium. Also contemplated, but less preferable, are other metals such as zinc, aluminum, and copper. The alkaline earth metals, such as magnesium metal, can be employed in a variety of shapes and sizes, for example as powder, granules, chips, or turnings; but, for the most efficaceous results, powder is recommended.

The values of x, y, and z in the formula $M_x{}^aM_y{}^b(M^cRR')_z \cdot nLB \cdot mM^dX$ are related by the valence of the metal $M^b$ in the following way:

$x+y=1.0$ and $z=x+(y$ multiplied by the valence of metal $M^b)$

Thus, for example, when metal $M^a$ is lithium and the metal $M^b$ is magnesium, the value of z, representing the amount of organoamide (or organophosphide) in the molecule will be equal to the value for x, i.e., the mole fraction of lithium metal (per total moles of Li and Mg), plus the mole fraction of magnesium times two (2.0).

In specific examples, the compounds $Li_{0.01}Mg_{0.99}(NR_2)_{1.99}$ and $Li_{0.99}Mg_{0.01}(NR_2)_{1.01}$ represent opposite ends of the mole fraction range for Li and Mg. The maximum value for z is thus 2.0 and the minimum value for z is 1.0, and these values occur when only the pure compounds $Mg(NR_2)_2$ and $LiNR_2$, respectively, are present.

The term LB in the formula $M_x{}^aM_y{}^b(M^cRR')_z \cdot nLB \cdot mM^dX$ stands for Lewis base, a polar, aprotic, non-reactive (to amide) organic compound which normally is assumed to associate with the metal organoamide in an amount equal to n moles per mole of metal organoamide, which value is generally less than four. Lewis base types contemplated in this invention are: acyclic and cyclic ethers such as dimethyl ether, diethyl ether, di-n-butylether, methyl-tert-butylether, tetrahydrofuran, 2-methyltetrahydrofuran, tetrahydropyran, 2-methyltetrahydropyran, 1,2-dimethoxyethane, 1,4-dioxane, diethylene glycol diethyl ether, and the like. Also contemplated are acyclic and cyclic tertiary amines such as trimethylamine, triethylamine, tri-n-butylamine, dimethyl-cyclohexylamine, N-methylpyrrolidine, N-methylpiperidine, N-methylmorpholine, N,N,N',N'-tetramethylethylenediamine, 2-dimethylaminoethyl-ethyl ether, and the like. Also contemplated are amines identical to those employed in the preparation of the metal organoamide compositions themselves (see above).

Also contemplated are hydrocarbon-soluble compounds of the type shown above which also contain complexed metal halides such as lithium chloride and bromide, generally represented by the formula $M_x{}^aM_y{}^b(M^cRR')_z \cdot nLB \cdot mM^dX$, where $M^d$ is an alkali metal, specifically lithium, X is halogen, generally chlorine, n is a number which when multiplied by z is greater than one and less than four, and m is a number between one and two.

The process for preparing such compositions may begin with the conversion of magnesium metal to a mono- or dialkylamidomagnesium halide as shown in equation 1 and described above, followed by admixture with lithium metal (finely divided) and reaction thereof with mono- or dialkylamine in the presence of styrene and sufficient LB (preferably tetrahydrofuran) to dissolve the attendant by-product lithium halide (generally chloride or bromide). As mentioned earlier, the amount of LB (THF) required to completely dissolve this lithium halide is generally equal to about two molar equivalents per mole of halide. Generally, the value of m in the above equation will not be greater than two.

Obviously, lithium halide salts such as lithium chloride or lithium bromide (anhydrous) may be added to the compositions of general formula $M_x{}^aM_y{}^b(M^cRR')_z \cdot nLB$, where n is sufficiently high, to dissolve them therein and to form the novel compositions of this invention. The value for x in the above general formula may be zero, whereupon the products of the invention are hydrocarbon solutions of magnesium bis-monoalkylamides and magnesium bis-dialkylamides containing dissolved (complexed) lithium halides. In like manner, the value for y in the above general formula may be zero, whereupon the products of the invention are hydrocarbon solutions of lithium monoalkylamide and lithium dialkylamides containing dissolved (complexed) lithium halides. The lithium halides alone have no solubility in hydrocarbon solvents containing limited amounts of Lewis base although lithium bromide, alone, is soluble in pure THF to the extent of approximately one-third of a mole per mole of THF. The following formulas describe some of the processes involved in the preparation of these compositions.

A. Preparation of $LiMg(NR_2)_3 \cdot nTHF \cdot mLiX$

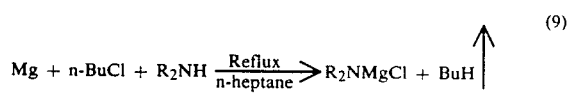  (9)

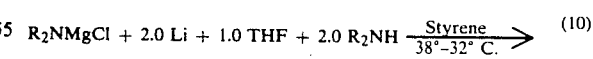  (10)

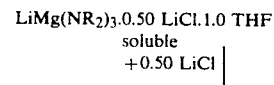

or with twice the amount of THF:

Step (1) Same as above.
Step (2):

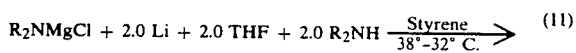  (11)

-continued

LiMg(NR$_2$)$_3$.LiCl.2.0 THF
soluble

B. Preparation of Mg(NR$_2$).nTHF.mLiX

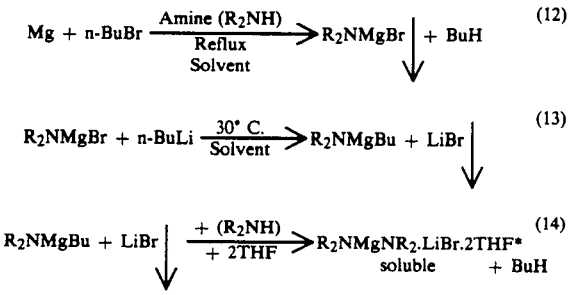

$$Mg + n\text{-}BuBr \xrightarrow[\text{Solvent}]{\text{Amine (R}_2\text{NH)} \atop \text{Reflux}} R_2NMgBr \downarrow + BuH \quad (12)$$

$$R_2NMgBr + n\text{-}BuLi \xrightarrow[\text{Solvent}]{30° C.} R_2NMgBu + LiBr \downarrow \quad (13)$$

$$R_2NMgBu + LiBr \downarrow \xrightarrow[+ 2THF]{+ (R_2NH)} R_2NMgNR_2.LiBr.2THF^* + BuH \quad (14)$$
soluble

*Note: The above solution product was found to be highly stable/soluble between 40° C. and 0° C. for more than 30 days.

C. Preparation of LiNR$_2$.nTHF.mLiX

LiN(iPr)$_2$+LiBr ↓ +2.5 THF→LiN(iPr)$_2$.LiBr.2.5 THF (15) solution in cyclohexane Solution concentration = 1.0M each in LiN(iPr)$_2$ and LiBr.

Group IIA (alkaline earth) metal organoamides, such as magnesium bis-diisopropylamide (MDA), can be prepared in a number of ways as described earlier. One key method involves (a) the reaction of magnesium metal with a mixture of n-butyl chloride and diisopropylamine in hydrocarbon solvent at reflux temperatures (the reflux temperature drops constantly during the addition due to release of n-butane) over a four hour period to form a slurry of diisopropylamidomagnesium chloride; (b) addition of lithium metal (sand or dispersion) followed by a mixture of diisopropylamine (25% of amine is in pot to start), tetrahydrofuran and styrene, first at 35°–40° (initiation of reaction), then at 30°±5° C. over a 2-3 hour period; and (c) filtration to give a clear solution of the product. Sodium dispersion can be used in place of the lithium metal in step (b). The initial reaction temperature of step (a) is generally the boiling point of the hydrocarbon solvent in which the reaction is taking place. Hydrocarbon solvents such as heptane, cyclohexane, or ethylbenzene are employed. As reaction progresses during the addition of alkyl halide and amine to the magnesium metal, the reflux temperature drops due to evolution of butane. Thus, for example, when heptane is the hydrocarbon solvent, the reaction temperature will drop from an initial value of about 98° C. to a value of about 60° C. After addition of reactants is complete, the mixture is stirred and kept at 60° C. for an additional 2-3 hours to complete the reaction. The resulting diisopropylamidomagnesium chloride is insoluble in the reaction medium. In step (b), lithium diisopropylamide is formed as an intermediate, which then reacts with the diisopropylamidomagnesium chloride to give the desired magnesium bis-diisopropylamide in solution and a precipitate of lithium chloride. It is useful to initiate the lithium metal reaction with styrene and diisopropylamine generally in the presence of a maximum of 0.5 molar equivalents of THF per mole of lithium and preferably less than 0.4, but more than 0.2 molar equivalents of THF/mole Li, most preferably between 0.3 and 0.4 molar equivalents of THF/mole Li at temperatures of about 40° C.; and then to carry out the remainder of the addition and post-addition reaction at somewhat lower temperatures in order to minimize side reactions. An overall reaction range is 0°–50° C. with a preferred range of 20°–40° C. and a most preferred range of 35°–40° C. The use of limited THF as described above results in the formation of halide-free solutions of the desired product. Should lithium-halide-containing solutions of MDA be desired, at least 0.5 molar equivalents of THF, and preferably at least 1-2 molar equivalents of THF per mole of lithium should be employed. Alternatively, n-butyllithium instead of lithium metal may first be reacted with diisopropylamidomagnesium halide, and the resulting n-butylmagnesium diisopropylamide reacted further with diisopropylamine in the presence of the desired quantity of THF to give either halide-free or halide-containing product. Overall, processing times under these conditions are generally less than 12 hours, with a most preferred period of four hours and under for each step of the reaction.

If an ether-free halide-free hydrocarbon solution of magnesium bis-diisopropylamide (MDA) is desired, then either a dialkylmagnesium, such as n-butyl-sec-butylmagnesium, is reacted directly with 2 molar equivalents of diisopropylamine; or the product of reaction (a) above is reacted first with n-butyllithium, then with diisopropylamine to convert the diisopropylamidomagnesium chloride to magnesium bis-diisopropylamide and the by-product lithium chloride filtered off. Such etherfree solutions of MDA show a limited solubility for the product (MDA), the maximum solubility being about 0.7–0.8 moles/liter at temperatures of 0°–30° C. Addition of 1 and 2 moles of THF, respectively, per mole of MDA allows for the preparation of MDA in hydrocarbon solutions in concentrations of at least 1 and 2 moles MDA per liter of solution, respectively. In any case, the use of a dialkylmagnesium compound to prepare MDA is less economical than the two step magnesium metallithium metal route described earlier.

Variation of the dialkylamine employed in reaction (a) above in certain cases results in the direct formation of the desired magnesium bis-diorganoamide. Thus, for example, utilization of >2 molar equivalents of di-n-hexylamine in place of diisopropylamine in the direct reaction of magnesium metal with n-butyl chloride gives a viscous hydrocarbon solution of magnesium bis-di-n-hexylamide and insoluble MgCl$_2$. It is believed that the longer chain (C$_5$ and higher) dialkylamines yield somewhat more soluble intermediate dialkylamidomagnesium chlorides which allow the reaction to proceed further to the desired bis-dialkylamides, whereas the lower chain (<C$_5$) dialkylamines do not.

The above-described Group IIA metal bis-organoamides, such as magnesium bis-diisopropylamide, can be utilized further to prepare the hydrocarbon-soluble bimetallic Group IA/IIA metal organoamides of the present invention.

However, in the presence of 1.5±0.5 moles of tetrahydrofuran per mole of organoamide, the soluble amide concentration of such Li$_x$Mg$_y$(N(iPr)$_2$)$_z$ compositions could be increased to 2.0 molar and above, and these solutions were stable to further precipitation with time. It has now been found possible to economically prepare such hydrocarbon-soluble solutions of Li$_x$Mg$_y$(NR$_2$)$_z$ in which $x+y=1$ and $z=x+2y$, via novel routes.

One such economical route is useful if the resultant x/y ratio in the $Li_xMg_y(NR_2)_z$ composition is held below about 0.3. For example, diisopropylamidomagnesium chloride is first prepared as a hydrocarbon slurry as described above from magnesium metal, n-butyl chloride, and diisopropylamine. Next, lithium metal in the form of a dispersion of finely divided particles [1.3 moles Li/mole(iPr2N)MgCl] is added to the slurry held at about 40° C. To the slurry is then added, dropwise, a solution of styrene (~0.5 mole/mole Li), diisopropylamine (~1 mole/mole Li) and tetrahydrofuran (~0.3 mole/mole Li) to form LDA, keeping the reaction temperature generally in the range of 20°–40° C., and most preferably in the range of 30°–35° C. The resultant solution is filtered away from the by-product LiCl salt which is totally insoluble in the medium. The ratio of THF to LiCl in the final product composition is thus held well below 0.5, and no solubilization of LiCl by the THF occurs at the THF/LDA (1.0±0.2) ratios necessary to promote the LDA formation.

However, when x/y ratios in the $Li_xMg_y(NR_2)_z$ product above about 0.3 are sought, preformed MDA, free of by-product LiCl, should be employed in place of diisopropylamidomagnesium chloride, in order to avoid solubilization of by-product LiCl by the greater amount of THF required to promote the formation of the larger proportionate amount (to MDA) of LDA. The use of preformed MDA in this case is a two pot reaction and therefore is more expensive than the one pot synthesis described above. As mentioned earlier, the THF requirement to obtain higher than a 1.5 molar amide concentration in hydrocarbon solutions is about 1.0 mole THF per mole of amide. Thus, solubility of the compositions $Li_xMg_y(NR_2)_z$ in hydrocarbons, where x/y is <0.5, will be limited by the smaller amount of THF utilized in the diisopropylamidomagnesium chloride route to prevent LiCl solubilization. The halide-free MDA route to $Li_xMg_y(NR_2)_z$ has no such limitation, and halide-free organoamide concentrations of these compositions of 2.0M and higher are readily achieved. As described earlier, the limitation on x/y ratio can be eliminated by the use of sodium metal in place of lithium in the preparation of precursor diisopropylamidomagnesium chloride, since NaCl by-product is not solubilized by THF/LDA levels of 1.0 or higher. The Mg/Na/Li ternary metal route thus allows for an inexpensive one pot synthesis of $Li_xMg_y(NR_2)_z$ in hydrocarbon solutions at amide concentrations of 2.0M and above. Obviously, ternary metallic amide complexes can be made by variation of the proportions of the three metals involved.

When the x/y ratio in the product $Li_xMg_y(NR_2)_z$ is sufficiently high (>10), then the source of the MDA used in its preparation no longer contributes as significantly to the overall cost of the product. Thus, a $Li_{0.95}Mg_{0.05}(N(iPr)_2)_{1.05}$ composition can be readily prepared by first reacting n-butyl-sec-butylmagnesium in heptane (DBM, Lithco) with 2 molar equivalents of diisopropylamine, then adding lithium metal (sand or dispersion) followed by the dropwise addition of a mixed solution of THF, styrene, and diisopropylamine over a three hour period at 30°–35° C., and then a post-addition reaction period of one hour yielding a clear light-colored solution of the desired product after filtration. Preformed halide-free MDA solutions or an MDA+NaCl slurry which are less costly than DBM may also be used. Although lithium metal is employed as the most economical raw material for the formation of lithium diisopropylamide, it is understood that one may also employ organolithium compounds such as n-butyllithium, methyllithium, 2-ethylhexyllithium, ethyllithium, phenyllithium, etc., in the reaction with diisopropylamine, although they are more expensive to use than the metal.

Such $Li_xMg_y(NR_2)_z$ compositions in hydrocarbon solution containing somewhat more than 1 mole of THF/mole amide, where x/y = 19 or even higher, have now been prepared and unexpectedly have been found to be significantly more resistant to thermal decomposition than comparable $LiN(iPr)_2$ solutions containing ≦1 mole of THF/mole amide.

Surprisingly $LiN(i-Pr)_2$ hydrocarbon solutions containing about 1.5 moles THF/mole amide also possess an improved stability as compared to comparable $LiN(i-Pr)_2$ solutions containing one or less moles of THF/mole amide. It had been earlier reported in U.S. Pat. No. 4,595,779 that high levels of THF (2–6 moles THF/mole of amide) contributed to an escalating rate of decomposition (see cols. 3 and 4, Table I, sample numbers C and D; also see col. 4, lines 45 to 48). On the other hand it was shown in the same reference (col. 4, lines 48–61) that significantly lower decomposition rates were evident at THF/amide ratios of 1 and below. At THF/amide ratios of about 0.5, $LiN(i-Pr)_2$ product precipitated from solution (col. 4, lines 62 to 66) at 0° and 20° C. Thus, a useful range of THF/amide of 0.5 to 1.1 was claimed in this patent (see claim 22). Little or no information was presented to cover the intermediate range of 1.1 to 1.9 moles of THF/amide, except to show that there was no significant difference between ratios of 1.1 and 9.0 (Table I, F to J). It has now been established that THF/amide ratios in the range of 1.1 and 1.9, and more preferably in the range of 1.2 to 1.6 lead to a more stable (both thermal and precipitation) $LiN(i-Pr)_2$ product solution. For example, a 2.5 molar solution of $LiN(i-Pr)_2$ in heptane with an initial THF/amide ratio of 1.38 and also containing 7.7 mole percent free diisopropylamine (stabilizer) decomposed at a rate of 0.6% per day at 40° C. This can be compared to a loss of 1.16% per day (see entry sample number 0 in Table I of U.S. Pat. No. 4,595,779) for a comparable solution.

The major decomposition of LDA at THF/LDA ratios of 1.0 or less was found to be as follows:

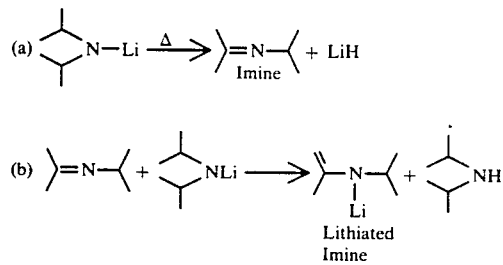

For example, at a THF/LDA ratio of 0.95 the loss of $LiN(i-Pr)_2$ by the above mechanism constitutes 100% of the total loss observed. Whereas, at a THF/LDA ratio of 1.38 the percentage loss by the above shown route was found to be only 35%. Thus, other modes of decomposition, perhaps involving metallation of THF and ethylbenzene, become the major routes to loss of product. This could readily account for the change (decreased rate) of loss of $LiN(i-Pr)_2$, since the above mechanism requires the consumption of two molar equivalents of LiN(i-Pr)$_2$ for every mole of product decomposed, while the other suggested moles of decomposition, i.e., metallation require only one.

Thermal stability testing of LDA and LDA containing 5 mole % MDA (LDA-1) in solution in a hydrocarbon solvent were carried out to determine the true rates of decomposition at three different temperatures. Details of this testing are summarized in the Table. Detection and quantitation of the lithiated imine formed on thermal decomposition as well as the presence of lithium hydride was verified.

Thermal stability at 0° and below

Thermal stability testing at 0° C. indicated both LDA and LDA-1 (LDA containing 5 mole % MDA), to be stable for at least 70 days. No imine and/or precipitation of hydride was detected in any of these samples. The still about three times higher than that of LDA-1 (Example 3; 0.45 mole % per day). The loss of active product due to precipitation from LDA-1 samples (Examples 3 and 6) is believed to be caused by an insufficient amount of THF and free diisopropylamine in these samples. As can be seen from Example 5, the average rate of decomposition was lower in Example 5 as compared to Examples 3 and 6 because of the above-mentioned condition.

Comparison of imine formation due to decomposition indicated LDA-1 (Example 6; 0.10 mole imine/kg solution) to be three times more stable than LDA (Examples 1 and 4; 0.33 and 0.32 mole imine/kg respectively).

Thus, the above results and data indicates that LDA-1 (containing about 5 mole % MDA) is significantly thermally more stable than LDA at any temperature between −20° C. to 40° C., especially between 15° C. and 40° C.

TABLE

Thermal Stability Comparison of LDA Vs. LDA Containing ~5 Mole % MDA (LDA-1) in Limited THF/Heptane Solvents at Various Temperatures

| Example No. | Product Name | Initial[a] Active Amide (M/kg) | MDA Conc. (M/Kg) | THF/LDA Mole Ratio | Free[b] Amine Mole % | Average Mole % Loss of Activity Per Day at Various Temperatures | | |
|---|---|---|---|---|---|---|---|---|
| | | | | | | 0 C. + 3[c] | 15 C. + 0.5[c] | 40 C. + 0.5 |
| 1 | LDA | 2.58 | 0.0 | 1.02 | 7.5 | 0.0 | 0.11 | 1.25[d] |
| 2 | LDA[f] | 2.76 | 0.0 | 0.89 | 5.4 | — | — | 1.16[d] |
| 3 | LDA-1 | 2.65 | 0.126 | 1.05 | 11.0 | 0.0 | 0.0 | 0.45[d][g] |
| 4 | LDA | 2.53 | 0.0 | 1.05 | 17.5 | — | — | 1.36[e] |
| 5 | LDA-1 | 2.44 | 0.121 | 1.13 | 20.0 | 0.0 | 0.0 | 0.22[e] |
| 6 | LDA-1 | 2.58 | 0.135 | 1.03 | 9.00 | 0.0 | 0.0 | 0.47[e][g] |

[a]W/E titration - corroborated by GLC analysis
[b]Free amine is diisopropylamine
[c]Mole % loss per day over a period of 70 days
[d]Mole % loss per day over a period of 28 days
[e]Mole % loss per day over a period of 14 days
[f]Data taken from Table 1, U.S. Pat. No. 4,595,779; Examples 1 and 4 were similarly prepared
[g]Precipitation of some magnesium noted at 40 C. after 14 days which caused higher rate of loss of total active amide.
Note:
Samples for Example Nos. 3, 5 and 6 (above) were prepared according to the procedure given in Example III B.1.

solubility of both LDA and LDA-1 is reduced at −20° C.±5° and crystalline solid product drops out, but which redissolved easily at room temperature in the case of LDA-1, whereas in the case of LDA it is hard to redissolve the solid crystals without shaking for a long time at room temperature. LDA-1 samples showed no crystallization (precipitation) at −20° C. when the THF to LDA mole ratio was 1.2 and higher.

Thermal stability at 15° C.±0.5°

LDA-1 samples (containing ~5 mole % MDA) showed improved thermal stability at milder temperatures (15° C.±0.5° C.) as compared to LDA. No decomposition or precipitation or imine formation were detected in LDA-1 samples (see Examples 3, 5 and 6) after testing for 70 days at 15° C. LDA (with no MDA) degraded at an average rate of 0.11 mole % per day during the same period (see Example 1). The loss was verified by detection of imine. All LDA samples became cloudy in appearance in one week's time. It was also noted that LDA solutions turned even more turbid at somewhat higher temperatures (20° C.±5° C.) whereas LDA-1 solutions remained clear.

Thermal stability at 40° C.±0.5°

Thermal stability testing at 40° C. indicated that after 14 days, LDA (see Example 4; 1.36 mole % loss per day) degraded six times more rapidly than LDA-1 (Example 5; 0.22 mole % per day). As expected, after 28 days at 40° C., the degradation rate of LDA (Example 1) slowed somewhat to 1.25 mole % per day but was The following examples further illustrate the invention. Unless indicated otherwise temperatures are in degrees C., percentages of reactants are in weight percent. All glassware was baked in an oven (150° C.) overnight, assembled, and purged until cool with argon. An inert argon atmosphere was maintained throughout reaction, filtration, and packaging. The metal amide concentration and compositions were determined by Total Base, Carbon metal bond assay (Watson Eastham titration and/or NMR), and Magnesium titration. The lithium and magnesium ratio is confirmed by Atomic Absorption Spectroscopy. The chloride content of solution was determined by Mohr titration. All lithium metal used contained 0.7% to 1.25% sodium.

EXPERIMENTAL

Example I

Preparation of Magnesium Bis-diisopropylamide (MDA)

A. Ether-Free Hydrocarbon Soluble MDA

1. Ether-free H.C. soluble MDA from dialkylmagnesium

One hundred sixty-five gms n-butyl-, sec-butyl magnesium (DBM) (20.8 wt % solution in n-heptane, 1.04 molar, 0.74 gm/ml density), was charged into a reaction flask under argon atmosphere. Thirty-four mls (0.2428 moles) of diisopropylamine was then added dropwise through an addition funnel to DBM under good agitation. Reaction temperature was maintained between 25°

C. and 59° C. (reflux). Product solution was then sampled for NMR and G.C. analysis to verify completion of the reaction. The reaction solution was then reacted further with an additional 34 mls (0.2428 moles) of diisopropylamine added between 25° C. and 53° C. (reflux) to form magnesium bis-diisopropylamide. The final solution product was sampled for NMR and G.C. analysis. The solution was found to contain 2.55 wt % Mg and was 0.80 molar in MDA. It contained 0.093 moles free amine/mole of MDA, yield 100%. The solution was stable to precipitation at room temperature and above, but some crystallization occurred at 0° to give a 0.7M solution.

2. Ether-free H.C. soluble MDA from Mg metal/n-BuLi route

Magnesium metal chips (12.0 gms, 0.494 mole), 0.20 gms iodine crystals, and 400 mls of n-heptane were charged into a glass reactor under argon atmosphere. The metal slurry was then heated to reflux (98° C.) for 60 minutes for activation of metal. n-Butylchloride (52 mls, 0.50 mole) and 70 mls of diisopropylamine were mixed in an addition funnel and added dropwise to the metal slurry at reflux temperature. Within a few minutes butane started refluxing, and reflux temperature dropped between 55° C. to 60° C. The reaction was completed at 55° C. to 60° C. in about three hours, and all metal chips had been converted into a fine white solid product in n-heptane solvent. No soluble magnesium was found in solvent. To this slurry 480 mls (0.48 mole) n-butyl lithium in n-heptane was added at 25-30° C. in about 30 to 40 minutes under good agitation, followed by addition of 70 mls (0.5 mole) of diisopropylamine. Stirring was continued for an additional 60 minutes before it was filtered to remove solids. About 890 mls of clear filtrate was obtained. The final solution (filtrate) was analyzed and found to contain 1.77 wt % Mg (0.48 molar MDA) and 0.143 mole free amine/mole MDA. Yield=90% concentration to 0.7M gave a highly stable solution between −20° and 40° C. (no loss for several months). Similarly, MDA in cyclohexane was prepared where n-BuLi in cyclohexane was used. The final filtrate was concentrated to 0.7 molar concentration by distillation of solvent, and it was found to be highly stable between 0° and 30° C. for more than 60 days.

3. Ether-free H.C. soluble magnesium bis-di-n-hexylamide from Mg metal/di-n-hexylamine reaction Magnesium metal chips (12.5 gm, 0.51 mole) 250 mls cyclohexane and 0.25 gm iodine crystals were charged first in one liter reaction flask and heated to reflux (80° C.) for 60 minutes for metal activation. n-Butylchloride (52 mls, 0.495 mole) was then added gradually to the reaction flask at reflux temperature, but no significant reaction with metal occurred, and therefore di-n-hexylamine (120 mls, 0.514 mole) was added to the reaction slurry. Reaction of metal with reagents was vigorous at reflux. Reflux temperature was seen dropping to 50° C. during this reaction. The reaction was continued for about three hours at reflux temperature. Almost all magnesium metal chips disappeared, and reaction slurry containing fine solids turned to a very viscous and not filterable condition. Next, 50 mls of cyclohexane and 58.6 mls of di-n-hexylamine was added gradually to thin the reaction slurry before being filtered. The final slurry was filtered well and yielded about 400 mls of clear yellow solution containing 0.6 molar Mg, 1.12 molar active amide, and traces of halide. Excess (free) amine was 1 mole per mole of MDA. Yield=90%. Solution was highly stable for months at 0° C. to room temperature.

B. Hydrocarbon Soluble MDA Complexed with Limited Amount of Ether (THF)

1. H.C. soluble MDA.nTHF from Mg metal/Li metal route

Magnesium metal chips (12.95 gm, 0.532 mole), 300 mls of n-heptane, and 0.25 gm pure iodine crystals were charged into the reaction flask under argon atmosphere and then heated to reflux temperature (98° C.±1.0°) for about an hour for metal activation. n-BuCl, 50 mls (0.478 mole) and 67.5 mls (0.48 mole), of diisopropylamine were mixed in an addition funnel and then added dropwise to the metal slurry in 90 minutes at reflux temperature (60°-98° C.). Reflux temperature was dropped constantly during addition of reactants due to release of butane. Reaction was continued for three more hours after completion of addition of reactants. The reaction slurry containing white fine solids was then cooled down to ≦40° C. To this slurry 3.20 gm (0.461 mole) of lithium metal sand was added at 35° C.±5° C., followed by dropwise addition of a mixture of 70 mls (0.5 mole) diisopropylamine, 13 mls (0.16 mole) THF and 27 mls (0.237 mole) styrene through an addition funnel, first at 38° C. for about 10 minutes and then at 25° C.±5° C. in two to three hours. The reaction slurry was then left overnight at 20° C.±5° C. under moderate stirring and argon atmosphere. The next morning hardly any lithium metal sand was found unreacted (nothing floating). The reaction slurry was then filtered to remove solid and a clear light yellowish solution filtrate was obtained. The product was analyzed: Wt % Mg=2.94, THF/MDA—0.33 MDA=0.91M, excess amine=0.1 mole/mole MDA, yield—90%. Similarly, MDA in cyclohexane was prepared.

2. H.C. soluble MDA.nTHF from dialkylmagnesium

The MDA solution, in ether-free hydrocarbon solvent made from the reaction of DBM with diisopropylamine as described earlier in I-A-1, was concentrated to 1.09 molar MDA from 0.70 molar by distillation of solvent under reduced pressure at ≦25° C. The concentrated 1.09 molar solution of MDA on standing produced some solid (precipitation) MDA, leaving 0.7 molar solution. The precipitated solids were found to be soluble in its mother solution at higher temperature (>25° C.). Adding one mole THF per mole of magnesium to this solution, no solid precipitation occurred on cooling to below 0° C. over one week. In another test it was found that the 2 mole THF per mole of MDA produces highly concentrated 2.2 molar MDA in n-heptane, excess amine=0.05 mole/mole MDA, THF/MDA=2.0, yield=100% which was also found to be highly stable between 0° and 40° C. At 40° C. in about 4-5 days, solution turned to dark reddish brown, but was clear.

3. H.C. soluble MDA.nTHF from Mg metal/Na metal route

Magnesium metal (12.50 gms, 0.51 mole), 0.3 gm iodine crystals, and 200 mls of n-heptane were charged into a one liter reaction flask under argon atmosphere.

The metal slurry was then heated to reflux (98° C.±1.0° C.) for 60 minutes to activate the surface of the metal.

The mixture of 74 mls (0.52 mole) diisopropylamine and 53 mls (0.51 mole) of n-butyl chloride was added dropwise to the metal slurry at reflux temperature in about two hours. The reflux temperature dropped to 60°–63° C. due to the release of butane from the reaction. The reaction slurry was allowed to stir at reflux temperature for three hours to complete the reaction. The slurry was left overnight under slow stirring and argon atmosphere at NTP. The next morning 10.35 gm (0.45 mole) Na metal was added to the reaction slurry at room temperature (22° C.). The slurry was heated to 38° C. and then reacted with a dropwise addition of a mixture of 50.8 mls (0.435 mole) styrene, 11.0 mls (0.135 moles) THF, and 70 mls (0.5 mole) DIPA. The reaction temperature was dropped by cooling bath to 30° C.±2° C. after 10 minutes of reaction at 38° C. The mix reagents were added to the pot in about 2.5 hours. The reaction slurry was left overnight under slow stirring and argon atmosphere. The next day the slurry was filtered to remove solids and a clear yellow solution (filtrate) was obtained. The clear solution product was analyzed and found to contain 3.20 wt % Mg (1.0M MDA), THF/MDA=0.31, excess amine=0.03 mole/-mole MDA, yield=97%. Solution was stable between 0° and 40° C.

Example II

Preparation of Lithium Magnesium Alkylamide Complex Compounds

A. Ether-free Hydrocarbon Soluble $Li_xMg_y(NR_2)_z$ Complex Compounds from Lithium and Magnesium Alkyls 1. $Li(NR_2)$: n-Butyllithium in cyclohexane (40 mls, 0.04 mole) was reacted with 12.5 mls (0.089 mole) diisopropylamine at <10° C. The temperature of the reaction mixture was then raised to 30° C. The solid LDA formation during low temperature reaction did not solubilize at 30°–35° C.

2. $Li_{0.33}Mg_{0.67}(NR_2)_{1.67}$: Ether-free cyclohexane soluble magnesium bis-diisopropylamide (75 mls, 0.0375 moles) was first charged into a reaction flask under argon atmosphere, followed by adding to it 3.0 mls (0.02143 mole) diisopropylamine. This solution was then reacted with dropwise addition of 9.0 mls (0.018 mole) n-butyllithium in cyclohexane at low temperature (10° C.) using cooling bath. Release of free butane during addition of butyllithium was seen. Clear solution product, without forming any solid, was obtained. The reaction product as solution remained clear for a couple of days. The analysis of the solution showed the presence of Li=0.21M, Mg=0.43M, Amide=1.07M, excess (free) amine=0.03 moles/mole Amide.

3. $Li_{0.50}Mg_{0.50}(NR_2)_{1.5}$: The above experiment (2) was repeated as described above, and then 3.0 mls (0.02143 mole) of additional diisopropylamine was added first followed by the addition of 9.0 mls (0.018 mole) of n-butyllithium at <1.0° C. The reaction mixture was stirred well at low temperature and then at 60 room temperature. No solid was formed. The clean solution product was found to be stable between 0° C. and room temperature for at least one day. The analysis of the product showed the presence of Li=0.36M, Mg=0.38M, Amide=1.12M, excess (free) amine=0.06 mole/mole Amide.

4. $Li_{1.67}Mg_{0.33}(NR_2)_{1.33}$: The above experiment (3) was repeated as described above, and then 6 mls (0.04285 mole) of diisopropylamine was added to it followed by adding 18 mls (0.036 moles) of n-butyllithium at <10° C. under good agitation. The reaction mixture continued stirring at room temperature for some time. The clear solution without forming any solid at room temperature was obtained. The solution product did form solid (precipitation) at <10° C. on cooling for some time. The analysis of this product showed the presence of Li=0.58M, Mg=0.305, Amide=1.20M, excess (free) amine=0.09 mole/mole Amide.

5. Stable and Soluble $Li_{0.67}Mg_{0.33}(NR_2)_{1.33}$ in H.C. Solvent Using Limited THF: Ninety grams of above prepared solution (4) was charged into a vacuum flask and then concentrated by distilling solvent at reduced pressure until 54.0 gm weight was attained. The concentrated solution turned hazy and, subsequently, turbid in a few minutes at room temperature.

The concentrated solution containing fine solids was turned into a thick slurry on cooling to 10° C. To this slurry 12 mls (0.146 mole) THF was added gradually under good agitation to obtain clean and clear solution. The clear solution product did not produce any solid between 0° C. and room temperature for about a week. The final solution had 1.86M active amide concentration. The analysis showed the presence of Li=0.91M, Mg=0.47M, Amide=1.86M, excess (free) amine=0.09 mole/mole of Amide.

B. Preparation of Soluble $Li_xMg_y(NR_2)_z.nTHF$ Complex in H.C. Solvent by Using Lithium Metal Route 1. $Li_{0.23}Mg_{0.77}(NR_2)_{1.77}.0.35THF$ in n-Heptane: Magnesium metal powder (12.0 gm, 0.493 mole), 0.25 gm iodine crystals, and about 560 mls of n-heptane were charged into a glass reactor under argon atmosphere. The metal slurry was heated to reflux temperature (98° C.±1.0) for 60 minutes for activation of metal. n-Butylchloride (51 mls, 0.49 mole) and diisopropylamine (70 mls, 0.5 mole) were mixed in an addition funnel, then added dropwise to the metal slurry at reflux temperature (98°–60° C.) over a period of 90 minutes. The reaction was completed at reflux in an additional two hours of stirring. The reaction slurry was changed into fine whitegray solids containing product in n-heptane. Next, the slurry was allowed to cool to around 40° C. by using outside cooling bath. To this slurry 4.7 gm (0.677 mole) of lithium metal was added. Next, 38 mls (0.332 mole) styrene, 100 mls (0.714 mole) diisopropylamine, and 17 mls (0.20 mole) THF were mixed in an addition funnel and then added dropwise to the reaction flask at 40° C. for 10–12 minutes to initiate the reaction of lithium metal with reagents. The reaction temperature was then maintained at 30° C.±5.0° C. by using a cooling bath for the remaining 2.5 hours of addition of reagents to the reaction flask. The reaction slurry was allowed to remain overnight under slow stirring at normal temperature (25° C.±5° C.). The next day the slurry was filtered to remove solids and recover clear yellow color filtrate. The volume of recovered filtrate was about 825 mls. The analysis of the solution product showed the presence of Li=0.156M, Mg=0.522M, Amide=1.20M, THF/Amide=0.20, yield=86%.

2. $Li_{0.34}Mg_{0.65}(NR_2)_{1.64}.1.62THF$ in n-Heptane: Magnesium bis-diisopropylamide in n-heptane (500 mls, 0.75 molar) was first charged into a one liter reaction flask followed by 2.1 gm (0.3 mole) lithium metal sand. To this slurry a mixture of 75 mls (0.9 mole) THF, 15.75 mls (0.13 mole) styrene, and 39 mls (0.28 mole) of diisopropylamine were added dropwise through an addition funnel at 35° C. for 5-10 minutes and then at 30° C. over a period of two hours. The reaction slurry continued to agitate for an additional two hours at room temperature. Next, the reaction slurry containing solid was filtered to remove solids and recovered approximately 575 mls of filtrate. The solution product was clear and had lemon yellow color. The analysis of this product showed the presence of Li=0.34M, Mg=0.65M, Amide=1.64M, THF/Amide=0.99, yield=86%.

3. $Li_{0.67}Mg_{0.33}(NR_2)_{1.33} \cdot 1.21THF$ in n-Heptane Solvent: Magnesium bis-diisopropylamide in n-heptane (333 mls, 0.70 molar) was first charged into a one liter flask followed by charging 4.2 gm (0.605 mole) lithium metal dispersion in n-heptane. Next, to this slurry a mixture of 76 mls (0.90 mole) THF, 28 mls (0.245 mole) styrene, and 78.6 mls (0.561 mole) of diisopropylamine was added dropwise through an addition funnel at 35° C., first for an initial 10 minutes and then at 30° C. over a period of two hours. The reaction slurry was allowed to agitate for two additional hours at room temperature. The reaction slurry was then filtered to remove solids and recovered approximately 600 mls of filtrate having light lemon yellow color. The analysis of the product showed the presence of Li=0.84M, Mg=0.38M, Amide=1.59M, THF/Amide=0.91, yield=90%.

4. $Li_{0.833}Mg_{0.167}(NR_2)_{1.167} \cdot 1.06THF$ in n-Heptane: Magnesium bis-diisopropylamides in n-heptane (166 mls, 0.75 molar) was first charged into a one liter reaction flask followed by adding 6.3 gm (0.908 mole) lithium metal and 70 mls of n-heptane. Next, to this slurry a mixture of 76.0 mls (0.90 mole) THF, 47 mls (0.41 mole) styrene, and 118 mls (0.84 mole) diisopropylamine was added dropwise through an addition funnel at 35° C. for 10 minutes to initiate the reaction, and then the reaction continued at 30° C. over a period of two hours. The reaction slurry was agitated for an additional two hours at room temperature before being filtered to remove solids. The resulting solution product (filtrate) was gold yellow in color and clear. The analysis of the product showed the presence of Li=1.38M, Mg=0.27M, Amide=1.89M, THF/Amide=0.91, yield=92%.

Example III

Preparation of Soluble Lithium Diisopropylamide:THF Complex in H.C. Solvent in the Presence of A Small Amount of MDA (Made by Using Dialkyl Mg/Mg Metal)

A. Preparation of Hydrocarbon Soluble LDA.THF Complex in Cyclohexane in the Presence of 10 Mole % MDA 1. LDA.THF Complex Containing 10% MDA by Alkyllithium: n-Butyllithium in cyclohexane (2.0 molar, 50 mls) was first charged into a reaction flask and then reacted with 14.5 mls (0.1036 mole) diisopropylamine at <10° C. On addition of diisopropylamine, the reaction mixture did produce a white solid precipitation of LDA. To this thick slurry 20 mls of 0.5 molar (0.01 mole) magnesium bis-diisopropylamide was added, and the slurry was stirred for 15 minutes. The reaction slurry turned into a clean solution. This clean solution which contained 1.19 molar Li, 0.119 molar Mg, and 1.43N active amide turned to turbid within a couple of days at <20° C. To this solution about 10 mls (0.12 mole) of THF was added, and on stirring turned back into a clean solution which remained stable between 0° C. and room temperature for more than a couple of weeks. Analysis of the product showed the presence of Li=1.06M, Mg=0.106M, Amide=1.28M, THF/Amide=0.99, yield=quantitative.

2. LDA.THF Complex in Cyclohexane Containing 10 Mole % MDA Made By Li Metal Route: n-Butyl-sec-butyl magnesium (DBM, 1.0 molar) in cyclohexane (100 mls) was first charged into a reaction flask along with an additional 150 mls of cyclohexane under argon atmosphere and then reacted with 30 mls (0.214 mole) diisopropylamine between 30° C. and 60° C. to form MDA. Next, to this reaction flask 5.8 gm (0.835 mole) lithium metal (sand) was added at 35° C. and then reacted by adding dropwise a mixture of 110 mls (0.786 mole) diisopropylamine, 78 mls (0.95 mole) THF, and 44 mls (0.384 mole) styrene, first at 38° C. for 10 minutes and then at 30° C. over a period of 2.5 hours. The reaction slurry was then left overnight at room temperature under slow stirring. The next morning the slurry was filtered to remove solids. The resulting clean filtrate (500 mls) having yellow color was analyzed. The product remained clear without any precipitation for a couple of months between room temperature and 0° C. The analysis of this product shows Li=1.48M, Mg=0.20M, THF/Amide=1.02, Amide=1.86M, yield=94.1%.

B LDA.THF Complex in H.C. Solvent Containing 5 Mole % MDA

1. Preparation of LDA.THF Complex in n-Heptane Containing 5 Mole % MDA (Made from DBM) by Lithium Metal Route: n-Butyl-sec-butyl magnesium (DBM) in n-heptane (57.5 mls, 1.05 molar) was first charged, along with an addition of pure 90 mls of n-heptane, into an oven dried one liter reaction flask equipped with a dropping funnel, mechanical stirrer, thermometer, and a condenser. Next, 40 mls (0.2857 mole) of diisopropylamine was added under controlled rate to the reaction flask to form soluble MDA between room and reflux temperatures. Then, the reaction flask containing MDA solution was charged with 10.0 gm (1.44 mole) of lithium metal (sand). The target concentration of the end product may be well controlled by the addition of hydrocarbon solvent. Next, the lithium metal slurry in MDA was reacted first at 40° C.±2.0° C. by dropwise addition of a mixed solution of 110 mls (1.36 mole) THF, 70 mls (0.61 mole) styrene, and 150 mls (1.07 mole) diisopropylamine. The reaction temperature was maintained between 35° and 40° C. by using dry-ice hexane cooling bath. After initiation of Li metal reaction, several attempts were made to drop the reaction temperature to 25° C., 10° C., and 0° C. by using a cooling bath; and still the rate of exothermic reaction was seen by rising temperatures. Finally, most of the reaction was carried out at room temperature (25° C.±2.0° C.). Addition rate of reactants was maintained and completed in three hours. The reaction slurry was allowed to agitate at room temperature for an additional one hour to complete the reaction. The reaction slurry containing reddish solid particles and unreacted excess lithium metal was then filtered to remove solids and yielded a yellow solution of LDA (~510 mls). The product was analyzed. The final product (solution) was found to contain 2.39N active amide and 0.05 mole Mg per mole of lithium. The product was tested for thermal stability at 0° C., room temperature, and 40° C. for more than 30 days. Analysis of the product showed Li=2.18M, Mg=0.11M, Amide=2.39M, THF/Amide 1.18, yield=90%.

Using the same method, two more runs were made, where in No. 1 (Exp. #6288) test ¼ of required DIPA and all styrene/THF were added through an addition funnel; and in No. 2 (Exp. #6292) all DIPA and 10% THF were added to the pot and 90% THF and all styrene were added through an addition funnel. Analyses of these products were as follows:

| 6288 | 6292 |
|---|---|
| Li = 1.85 M | 1.80 M |
| Mg = 0.12 M | 0.107 M |
| Amide = 2.10 M | 2.03 M |
| THF/Amide = 1.04 | 1.05 |
| yield = 90 | 87 |

C. Preparation of Soluble (1) MDA and (2) LDA.THF Complex in Hydrocarbon Solvent Containing 5 Mole % MDA Products Made from One Pot Reaction Using Mg/Na and Li Metals Magnesium metal powder (12.5 gm, 0.515 mole), iodine crystals (0.30 gm), and n-heptane (300 mls) were charged in a reaction flask and heated to reflux temperature for 60 minutes for metal activation. Next, a metal slurry was then reacted at reflux temperature with the dropwise addition of a mixture of 70 mls (0.5 mole) diisopropylamine and 50 mls (0.48 mole) n-butylchloride. The addition was completed in about 90 minutes. The reaction was completed at reflux temperature in about two additional hours of stirring. The grayish white slurry was then cooled down to 40° C. and then 11.0 gm (0.48 mole) Na metal was added. To this slurry a mixture of 55 mls (0.480 mole) styrene, 33 mls (0.40 mole) THF, and 66 mls (0.47 mole) diisopropylamine were added dropwise, first at 38° C. for 10 minutes and then the remaining mixture was added in 2.5 hours at 30° C. The reaction slurry was allowed to stir for an additional two hours at 30° C. and then filtered (leaving 75 mls slurry in the pot) to obtain a clean filtrate of MDA. The analysis of the MDA solution (709 mls including wash solvent) was found to be 0.57 molar Mg, 1.13N active amide, and traces of NaCl.

The reaction pot containing 75 mls of the above reaction slurry containing about 0.043 mole Mg as MDA and solid NaCl, unreacted metals, and other residual solid products, was charged with 7.5 gm (0.08 mole) Li metal and 150 mls n-heptane. The slurry was heated to 38° C., and then a mixture of 57 mls (0.50 mole) styrene, 140 mls (1.0 mole) diisopropylamine, and 82.0 mls (1.0 mole) THF were added dropwise to it in about 2.5 to 3.0 hours, first at 38° C. (10 minutes) and then at 28° C.±2° C. The slurry was left overnight under slow stirring at room temperature before being filtered the next morning. The filtrate was yellow orange in color. The analysis of this product shows Li=1.62M, Mg=0.086M, Amide=1.81M, IHF/Amide=1.05, yield=90%.

D. Preparation of H.C. Soluble LDA.THF Complex in Ethylbenzene/Heptane in the Presence of 3.75 Mole % MDA MDA (60 mls, 1.10 molar) in n-heptane containing 0.32 mole THF per mole of Mg was first charged under argon atmosphere into a one liter reaction flask. Next, 10.8 gm (1.56 mole) lithium metal (sand) was charged along with about 260 mls of ethylbenzene. The metal slurry was then heated to 40° C., and then 50 mls (0.62 mole) of THF and 100 mls (0.7143 mole) diisopropylamine were added to the reaction flask. The remaining 50 mls of THF (0.62 mole), 96 mls (0.69 mole) DIPA, and 76 mls (0.67 mole) styrene were mixed in an addition funnel and then added dropwise to the reaction flask at 40° C.±2° C. for the first 10 minutes and then at 30° C. over a period of 2.5 hours. The temperature of the reaction was maintained by using a dry-ice hexane cooling bath. The reaction slurry was then filtered after an additional three hours of stirring. The resulting filtrate yielded (~680 mls) as a clean, amber, reddish wine color solution of LDA. The analysis of this product shows the presence of Li=2.02M, Mg=0.075M, Amide=2.14M, THF/Amide=0.95, yield=94%.

Example IV

Preparation of H.C. Soluble Lithium di-n-Butylamide.THF Complex Containing 5 Mole % Magnesium Bis-di-n-Butylamide in n-Heptane Di-n-sec-butylmagnesium (28.5 mls, 1.05 molar) in n-heptane was first charged under argon atmosphere into a 500 ml reaction flask. Next, to it di-n-butylamine (10 mls, 0.07 mole) was added dropwise with good agitation between room and reflux temperatures (25° C. to 60° C.) to form soluble magnesium bis-di-n-butylamide. To this reaction flask 100 mls of n-heptane and 4.52 gm (0.65 mole) lithium metal were charged at 35°–40° C. The metal slurry in magnesium bis-di-n-butylamide was allowed to stir at 40° C. for one hour. The target concentration of the end product may be well controlled by the addition of a calculated quantity of hydrocarbon solvent. Lithium metal slurry was then reacted first at 35° C.±2° C. by dropwise addition of a mixed solution of di-n-butylamine (105 mls, 0.623 mole), styrene (33 mls, 0.29 moles), and THF (45 mls, 0.55 moles). The reaction temperature was varied from 0° C. to 35° C., and still the rate of reaction was maintained good (even at lower temperatures). Finally, reaction temperature was maintained at 30° C.±5° C. by using a cooling bath. The addition of reactants was completed over a period of 2.5 hours and was allowed to react for one additional hour to complete the reaction. The reaction slurry containing a white silky solid were found at the end of the reaction period. Solid, silky, white precipitation may have occurred due to not having enough THF to obtain a soluble product. An additional 13 mls (0.16 mole) THF was then added under good agitation to dissolve most of the shiny, silky solids present in the slurry. After two hours of stirring at 30° C. the slurry was filtered to remove suspended solid and unreacted excess lithium metal and yielded a yellow solution of lithium di-n-butylamide containing magnesium bis-di-n-butylamide. The final volume of the filtrate was close to 305 mls. The clean filtrate did produce precipitation on cooling at 0° C. overnight. Therefore, an additional 13 mls of THF (0.16 mole) were added to it to obtain a thermally stable solution at 0° C.±3° C. for a few weeks. The analysis of this solution showed Li=1.62M, Mg=0.094M, Amide=1.81M, THF/Amide=1.51, yield=94%.

Example V

Preparation of H.C. Soluble Lithium Pyrrolidide.THF Complex Containing 5 Mole % Magnesium di-Pyrrolidide by Li Metal Route Di-n-sec-butylmagnesium (60 mls, 1.23 molar) in cyclohexane was first charged under argon atmosphere into an oven dry one liter reaction flask. Next, 150 mls cyclohexane and 15 mls (0.180 mole) pyrrolidine were added dropwise under good agitation between 25° C. to 60° C. The reaction slurry was allowed to stir at 55° C.±5° C. for 45 minutes to form magnesium di-pyrrolidide which is an insoluble white solid. The slurry temperature was brought back to 40° C. by using a cooling bath, and then 12 gms (1.73 mole) of lithium metal as dispersion in cyclohexane was charged to the reaction flask. The targeted 2.0 molar concentration of the final product solution was well controlled by adding the required volume of cyclohexane. Next, the reaction slurry containing lithium metal and magnesium di-pyrrolidide was reacted at 38° C. (for 10 minutes) and then at 30° C. (2.5 hours) by dropwise addition of a mixed solution of THF (125 mls, 1.525 mole), pyrrolidide (125 mls, 1.5 mole), and styrene (85 mls, 0.74 mole). The color of the reaction slurry remained grayish, and the slurry turned thinner due to dissolution of solid magnesium di-pyrrolidide with the formation of a lithium compound. The reaction slurry was left overnight at 20° C.±5° C. under slow stirring. The next morning it was filtered to remove solid and yielded a clear yellow solution product. The total volume of the filtrate was 745 mls having 2.03N active amide concentration. Analysis of this solution showed Li=1.79M, Mg=0.105M, Amide=1.99M, THF/Amide=102, yield=91%.

Example VI

Preparation of H.C. Soluble Lithium Hexamethyldisilazade.THF Complex in n-Heptane in the Presence of 5 Mole % Magnesium di-Hexamethyldisilazide Di-n-sec-butylmagnesium (50 mls, 1.05 molar) in n-heptane was first charged along with fresh 125 mls of n-heptane into a one liter reaction flask under argon atmosphere and then reacted with 25 mls (0.118 mole) hexamethyldisilazane between 30° C. and 86° C. (reflux) for about 45 minutes. Next, 8.6 gms (1.24 mole) lithium metal (dispersion) were added at 30° C. Next, the lithium metal slurry was reacted first at 40° C.±2° C. for 15 minutes with the dropwise addition of a mixture of styrene (65 mls, 0.567 mole), THF (180 mls, 2.19 mole), HMDS (255 mls, 1.21 mole), and then at 30° C. over a period of three hours. The reaction slurry was allowed to complete the reaction by stirring for an additional three hours at room temperature (25° C.±3° C.) before being filtered. The resulting filtrate yielded (895 mls) as a clean solution of LHS having light lemon yellow color. The analysis of this product showed Total Amide=1.13M, Mg=0.0575M, THF/Amide=2.64, Yield=80%. The LHS:THF complex was made in pure THF medium with and without magnesium under identical method as described above. The analysis of these two runs is shown below:

| With Magnesium | Without Magnesium |
|---|---|
| Active Amide = 1.47 M | 1.50 M |
| Mg = 0.072 M | — |
| THF/Amide = 4.7 | 5.2 |
| yield = 92% | 92% |

Example VII

Preparation of H.C Soluble Sodium Magnesium Tri Diisopropylamide in Cyclohexane by Mg/Na Metal Route

A. $Na_{0.285}Mg_{0.714}(NPr_2^i)_{1.713}.0.31THF$

Magnesium metal chips (10.02 gm, 0.412 mole) iodine crystals (0.2 gm) and cyclohexane (500 mls) were charged into a one liter reaction flask and heated to reflux (80° C.) under argon atmosphere for about one hour for activation of metal. Next, n-butyl chloride (42 mls, 0.401 mole) and diisopropylamine (60 mls, 0.428 mole) were added as mixed solution at a controlled rate under good agitation. The addition of this mixed solution was completed over a period of 90 minutes. The reaction slurry was allowed to stir at reflux for an additional two hours to complete the reaction. The reaction slurry containing a white solid ($R_2NMgCl$) was then cooled to 30° C. About 20.0 gms of sodium metal dispersion made from Na metal chunk was then added to the reaction slurry. Next, the reaction slurry was then reacted with a dropwise addition of a mixed solution of styrene (60 mls, 0.52 moles), THF (15 mls, 0.1786 mole), and diisopropylamine (95 mls, 068 mole) through an addition funnel at 35° C. The reaction temperature started rising on addition of about 10 mls of mixed solution. The reaction temperature was maintained at 35° C. by using cooling bath during three hours of addition time. The slurry was allowed to stir at 35° C. for an additional two hours to complete the reaction and then filtered to remove solids. The resulting filtrate yielded 810 mls as a clear yellow solution. The analysis of this product shows Na=0.20M, Mg=0.50M, Amide=1.21M, THF/Amide=0.18.

B. $Na_{0.5}Mg_{0.5}(NPr_2^i)_{1.5}.1.245THF$

This preparation was carried out by the same method as described in (A) using the following raw materials in order of addition:

Magnesium metal chips (10.0 gm, 0.411 mole); n-butyl chloride (40 mls, 0.383 mole); diisopropylamine (60 mls, 0.428 mole); iodine crystals (0.2 gm); cyclohexane (500 mls); sodium metal (20 gm); styrene (95 mls, 0.83 mole); THF (80.0 mls, 0.976 mole); diisoproylamine (115 mls, 0.8215 mole).

The analysis of this product showed Na=0.47M, Mg=0.43M, Amide=1.38M, THF/Amide=0.83.

Example VIII

Preparation of $Li_xMg_y(NR_2^i)_z.nTHF.mLiCl$ in Heptane

Magnesium metal (12.95 gm, 0.533 mole), 800 mls n-heptane, and 0.25 gm iodine crystals were charged into the reaction flask under argon atmosphere and then heated to reflux temperature (98° C.±1.0° C.) for about 60 minutes for metal activation. n-BuCl, 50 mls (0.478 mole) and 70 mls (0.5 mole), of diisopropylamine were mixed in an addition funnel and then added dropwise to the metal slurry at reflux temperature (60°–98° C.). Reflux temperature was dropped constantly during addition of reactants. After three hours of stirring the reaction slurry containing white fine solids was then cooled down to 38° C. To this slurry 6.98 gm (1.0057 mole) of lithium metal sand was added, followed by dropwise addition of a mixture of 40 mls THF (0.4915 mole), 57 mls styrene (0.5 mole) and 140 mls (1.0 mole) diisopropylamine through an addition funnel, first at 38° C. for about 15 minutes and then at 32° C.±2° in 2.5 hours. The reaction slurry was then left stirring at room temperature for overnight. The next morning hardly any lithium metal was found unreacted (nothing floating). The reaction slurry containing solid was then filtered to yield yellow solution. The analysis of this product showed to contain 0.45 molar magnesium, 0.6705 molar lithium, 1.6 molar active amide and 0.228 molar chloride.

Example B

Part of the above final slurry was treated with an additional one equivalent THF, solubilized all solid LiCl into product solution--obtained by filtration to remove some turbid solids.

Example IX

Preparation of Mo(NPr$^1$)$_2$.LiBr.2THF in Cyclohexane

Magnesium metal granular powder (12.165 gm, 0.5 mole), 450 mls of cyclohexane and 0.3 gm iodine crystals were charged into the reaction flask under argon atmosphere and then heated to reflux temperature (80° C.±1.0°) for about one hour for metal activation. n-Butylbromide (n-BuBr), 54 mls (0.5 mole) was then added to the reaction flask at reflux temperature through an addition funnel but no significant amount of reaction between metal and n-BuBr was seen, 70 mls (0.5 mole) diisopropylamine was then added drop by drop to the reaction flask in about 45 minutes at reflux temperature. Immediately reaction started vigorously with the release of butane and reflux temperature was seen dropping constantly during addition. Reaction was continued for three hours at reflux and three hours at room temperature. The reaction slurry containing white fine solids was then left overnight under slow stirring at room temperature. The next morning 290 mls (0.5 mole NBL) of n-butyl lithium in cyclohexane was added dropwise to the reaction slurry at 30° C.±2° C., followed by addition of 70 mls (0.5 moles) of diisopropylamine and 75 mls (0.92 mole) of THF. The rise in temperature of the reaction slurry was noted due to the formation of magnesium bis-diisopropylamide and lithium bromide. The reaction slurry was stirred for about 60 minutes at room temperature. The reaction slurry containing a small amount of fine suspended particles was filtered to yield a clear yellow (gold) color solution product. The final volume of the filtrate yielded to 990 mls.

The product was analyzed: 0.462 molar total magnesium, 0.5 molar lithium, 0.5 molar bromide, 0.95N active amide and 0.925 molar THF. The formula of product derived from the analysis is Mg(NiPr$_2$)$_2$. LiBr.2THF.

Example X

Preparation of Soluble LiN(iPr)$_2$.LiBr.2.5 THF Complex in Cyclohexane 50.0 mls of 2.0 Molar clear LDA.THF in cyclohexane was charged into a bottle containing 8.703 gms of anhydrous LiBr and a magnetic stirrer. This mixture (slurry) was stirred for 30 minutes at room temperature, and did not dissolve any significant amount of solid. 35 mls of cyclohexane was added to dilute, but no more solid dissolved. 4.1 mls (0.05 mole) THF was then added dropwise under good agitation for 30 minutes. Some solid (about 25%) dissolved. Another 4.1 mls THF was added and stirred for 30 minutes, which dissolved even more of the LiBr solid. But still about 25% of the solid was left undissolved after an additional 30 minutes stirring. An additional 4.3 ml THF was added and the mix stirred for another 30 minutes and found to dissolve more than 90% of the solids, leaving a hazy (turbid) solution.

Turbidity and hazyness may be due to impurities in the anhydrous LiBr, because LiBr solubility in THF (0.32 mole LiBr/mole of THF) showed the same kind of turbidity.

The foregoing examples illustrate some of the product variations covered by the general formula

wherein M$^a$, M$^b$, M$^c$, M$^d$, R, R', x, y, z, n and m have the meaning ascribed to them where this formula first appears herein above. The examples illustrate preferred compositions within preferred molar ranges defined by selected values of x, y, z, n and m. One preferred group of compositions contain no lithium halide, i.e., m is zero; in these compositions the value of x is between 0.01 to 0.99, the value of y is between 0.99 to 0.01, z equals x+2y and n is a number which when multiplied by z has a value greater than zero and less than three. In another group of lithium halide-free compositions x is a number between 0.8 and 0.99, y is between 0.2 and 0.01, z equals x+2y, n equals z multiplied by a number between 1 and 2. Compositions containing lithium halide require an additional 2 moles of Lewis base such as THF for each mole of lithium halide in the compositions. When x is zero and m is between zero and two, n is between zero and four. When both x and y are greater than zero and m is greater than zero and not more than two, n is equal to m multiplied by x+2 (n=m(x+2)). When y is zero, x is 1 and m is greater than zero and equal to or less than two, n is equal to m multiplied by 2 plus one, n=2m+1.

What is claimed is:

1. An alkali metal diorganoamide consisting essentially of compositions of the formula:

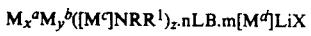

wherein M$^a$ is selected from lithium, sodium, potassium and mixtures thereof; M$^b$ is selected from magnesium, calcium, barium, and strontium, R and R' are independently selected from alkyl groups of 1 to 10 carbon atoms, cycloalkyl groups of 4 to 10 carbon atoms, aryl groups of 6 to 10 carbon atoms, alkylaryl groups of 7 to 12 carbon atoms, trialkylsilyl groups with alkyl groups of 1 to 5 carbons atoms, heteroalkyl groups of nitrogen, oxygen and silicon containing 3 to 10 carbon atoms and heteroaryl groups of nitrogen and silicon containing 6 to 12 carbon atoms and hydrogen; X is selected from chlorine, bromine, and iodine; LB is a Lewis base selected from alkyl ethers, cycloalkyl ethers, monoalkylamines, dialkylamines, tertiary alkylamines, cycloalkylamines and mixtures thereof; and x, y, z, n, and m represent defining molar proportions of each in relation to the whole, such that x+y=1 and the value of x is between 0.01 and 0.99 and the value of y is between 0.99 and 0.01, z=x+2y, n is a number which when multiplied by z is greater than zero but less than four, and m is a number from zero to two and a solvating amount of a liquid hydrocarbon solvent.

2. A composition according to claim 1 in which $M^a$ is selected from lithium, sodium and mixtures thereof, $M^b$ is magnesium, R and R' are independently selected from alkyl groups of 1 to 10 carbon atoms and hydrogen so that when one of R and R' is hydrogen, NRR' is a monoalkylamine and when R and R' are both alkyl groups, NRR' is a dialkylamino group, and LB is selected from cycloalkyl ethers, monoalkylamines, dialkylamines and mixtures thereof, and m is zero.

3. A composition according to claim 1 in which $M^a$ is selected from lithium, sodium and mixtures thereof, $M^b$ is magnesium, R and R' are both isoalkyl groups containing three carbon atoms so that NRR' taken together is diisopropylamino, LB is selected from the cycloalkyl ether, tetrahydrofuran, the dialkylamine diisopropylamine and mixtures thereof, the value of x is between 0.01 and 0.99, the value of y is between 0.99 and 0.01, and n is a number which when multiplied by z is greater than zero but less than three.

4. A composition according to claim 3 in which the value of x is between 0.80 and 0.99, the value of y is between 0.01 and 0.20 and n is z multiplied by $1.5 \pm 0.5$.

5. A composition according to claim 1 in which $M^a$ is lithium, X is selected from chlorine and bromine, $M^b$ is magnesium, NRR' is diisopropylamine, Lb is selected from the cycloalkyl ether tetrahydrofuran and mixtures of tetrahydrofuran with the dialkylamine, diisopropylamine, x is 0.8 to 0.99, y is 0.2 to 0.01, n is m multiplied by two plus the value of x, and m is greater than zero but not greater than two.

6. A composition according to claim 3 in which the value of x is between 0.90 and 0.99 and the value for y is between 0.1 and 0.01.

7. A composition according to claim 3 in which x is 0.95 and y is 0.05.

* * * * *

UNITED STATES PATENT AND TRADEMARK OFFICE
CERTIFICATE OF CORRECTION

PATENT NO. : 5,002,689

DATED : March 26, 1991

INVENTOR(S) : Vijay C. Mehta; Terry L. Rathman; Conrad W. Kamienski; Robert C. Morrison; Randy W. Hall It is certified that error appears in the above-identified patent and that said Letters Patent is hereby corrected as shown below:

Column 3, line 29, insert "." between chloride and The.  Column 5, lines 4-9, delete " $\cong$ " and replace with -- $\leq$ --.  Column 10, line 32, "etherfree" should read --ether-free--.  Column 12, line 12, delete " $\cong$ " and replace with -- $\leq$ --; lines 16 and 17 should be one sentence.  Table (columns 13 and 14), footnote (g), "40 C" should read --40°C--.  Column 16, line 25, delete " $\cong$ " and replace with -- $\leq$ --; line 48, delete " $\cong$ " and replace with -- $\leq$ --.  Column 18, line 33, "$Li_{0.23}Mg_{0.77}(NR_b{}_2)_{1.77} \cdot 035THF$" should read --$Li_{0.23}Mg_{0.77}(NR_2)_{1.77} \cdot 0.35THF$--.  Column 25, line 23, "$Mg(NPr_2{}^i)_2 \cdot LiBr \cdot 2THF$" should read --$Mg(NPr^i{}_2)_2 \cdot LiBr \cdot 2THF$--

Column 26, line 47, claim 1, "$M^a{}_x M^b{}_y ([M^c]NRR^1)_z \cdot nLB \cdot m[M^d]LiX$" should read --$M^a{}_x M^b{}_y (NRR^1)_z \cdot nLB \cdot mLiX$--.

Signed and Sealed this

Twenty-fourth Day of November, 1992

Attest:

DOUGLAS B. COMER

Attesting Officer

Acting Commissioner of Patents and Trademarks